United States Patent
Gammon

(10) Patent No.: US 10,682,481 B2
(45) Date of Patent: Jun. 16, 2020

(54) ATTACHMENT FOR A TRACHEAL DEVICE

(71) Applicant: Claudine Gammon, Richmond, CA (US)

(72) Inventor: Claudine Gammon, Richmond, CA (US)

( * ) Notice: Subject to any disclaimer, the term of this patent is extended or adjusted under 35 U.S.C. 154(b) by 422 days.

(21) Appl. No.: 15/363,910

(22) Filed: Nov. 29, 2016

(65) Prior Publication Data
US 2018/0147379 A1 May 31, 2018

(51) Int. Cl.
*A61M 16/04* (2006.01)
*A61M 16/08* (2006.01)

(52) U.S. Cl.
CPC .... *A61M 16/0465* (2013.01); *A61M 16/0402* (2014.02); *A61M 16/0488* (2013.01); *A61M 16/0497* (2013.01); *A61M 16/0816* (2013.01)

(58) Field of Classification Search
CPC .......... A61M 16/0425; A61M 16/0402; A61M 16/0816; A61M 16/0488; A61M 25/02; A61M 2025/022; A61M 2025/026
See application file for complete search history.

(56) References Cited

U.S. PATENT DOCUMENTS

| | | | |
|---|---|---|---|
| 4,325,366 A | 4/1982 | Tabor | |
| 5,201,309 A | 4/1993 | Friberg et al. | |
| 5,616,116 A | 4/1997 | Born | |
| 5,947,121 A | 9/1999 | Marshall | |
| 6,009,872 A * | 1/2000 | Delaplane | A61M 16/0488 128/207.17 |
| 6,668,831 B1 | 12/2003 | Hegwood | |
| 7,195,016 B2 * | 3/2007 | Loyd | A61M 16/0465 128/200.24 |
| 2004/0226564 A1 * | 11/2004 | Persson | A61M 16/0465 128/207.14 |
| 2011/0146689 A1 * | 6/2011 | Curley | A61M 16/04 128/207.14 |
| 2011/0290254 A1 * | 12/2011 | Waldron | A61M 16/0465 128/207.14 |
| 2013/0220333 A1 * | 8/2013 | Morris | A61M 16/0497 128/207.17 |

FOREIGN PATENT DOCUMENTS

| | | | |
|---|---|---|---|
| EP | 0370962 A2 | 5/1990 | |
| EP | 2008680 A1 | 12/2008 | |
| WO | 9105579 | 5/1991 | |
| WO | WO-2013068047 A1 * | 5/2013 | ........ A61M 16/0465 |

OTHER PUBLICATIONS

Patent Translate: translation of WO 2013/068047 A1, Aug. 5, 2019 (Year: 2013).*

* cited by examiner

*Primary Examiner* — Nilay J Shah
(74) *Attorney, Agent, or Firm* — Vierra Magen Marcus LLP

(57) ABSTRACT

A tracheal tube attachment for a tracheal device is disclosed. The tracheal tube attachment includes a tube and a plate. The tube includes a bend provided to prevent water from entering into the tracheal tube attachment and tracheal tube. The tube includes a proximal section having an open proximal end for attaching to a tracheal device, and a distal section having an open distal end.

18 Claims, 5 Drawing Sheets

ATTACHMENT FOR A TRACHEAL DEVICE

BACKGROUND

Diseases such as larynx cancer can lead to an obstruction in the nose, mouth, or the upper portion of the windpipe, making it difficult for a person to breathe. In these cases, it may be necessary to create a by-pass air passageway in the person's neck using a tracheal device, such as a tracheostomy tube. The tracheostomy tube is inserted through a stoma in the person's neck and into the trachea to connect the trachea with air outside the person's body.

Given that a person would breathe in air via a tracheostomy tube, there is a risk that unwanted materials, such as water and other debris, may also fall in via an opening in the tracheostomy tube and interfere with the person's breathing. This is a particular problem when the person is taking a shower since it can be difficult for a person to breathe comfortably via a tracheostomy tube when there is a constant downward flow of water.

Tracheal tube attachments are contemplated in the prior art. Examples include U.S. Pat. No. 4,325,366 to Tabor; U.S. Pat. No. 5,201,309 to Friberg; U.S. Pat. No. 5,616,116 to Born; U.S. Pat. No. 5,947,121 to Marshall; and U.S. Pat. No. 6,668,831 to Hegwood. These references disclose simple structural configurations such as tubes and/or plates that may cover the opening of a tracheal device and may direct the flow of water around and away from the opening.

However, these references have numerous deficiencies. First, there is still a risk that unwanted materials may be sucked into the tracheal device via the tracheal tube attachment. The references do not disclose a tube having an increasing diameter for reducing the suction force on unwanted materials while simultaneously increasing airflow. Second, it may be possible for unwanted materials to get into the tracheal device through gaps around the area where the tracheal tube attachment connects with the tracheal device. There may also be gaps in between different components of the tracheal tube attachment where they connect to each other. The references do not disclose a tracheal tube attachment that is a single integrally connected piece and that has a plate for providing additional cover around the opening of a tracheal device.

SUMMARY

The present technology provides a new and improved solution to numerous problems experienced by persons with tracheal devices. A basic concept of the present technology is to provide a tracheal tube attachment for a tracheal device to prevent water and other unwanted materials from entering the tracheal device and into a person's trachea.

The tracheal tube attachment essentially comprises a hollow tube having an open proximal end and an open distal end. The tube may further include a proximal section connected to the proximal end, and a distal section connected to the distal end. The proximal and distal sections are connected to each other at an intermediate point. The proximal section may extend horizontally and have a consistent diameter along its length. The proximal section may be dimensioned for attaching the proximal end to a tracheal device. The distal section may extend at a downward angle of between zero and 90 degrees relative to the orientation of the proximal section. The distal section may have a diameter beginning with the same diameter as that of the proximal section at the intermediate point and increasing towards the distal end.

The proximal end may be integrally connected to the center of a plate. The plate may have a circular hole in the center receiving the proximal end so as to not block the opening of the proximal end.

DETAILED DESCRIPTION

The present technology includes a tracheal tube attachment used by a person having a tracheal device, such as a tracheostomy tube, fitted through a stoma in the person's neck and extending into the person's trachea. In embodiments described below, the tracheal tube attachment may be worn in the shower, while bathing in general, or in the rain to prevent falling water from entering a tracheal device where the water can then enter and impair a person's lungs. However, it is understood that the tracheal tube attachment described herein may be used in any of a variety of scenarios where it is desirable to keep falling debris, particulates, contaminants or other materials from entering the tracheal tube. Examples of such additional scenarios include face washing, face shaving and makeup application and removal. Other scenarios are contemplated.

The terms "top" and "bottom," "upper" and "lower" and "vertical" and "horizontal," and forms thereof, as may be used herein are by way of example and illustrative purposes only, and are not meant to limit the description of the present technology inasmuch as the referenced item can be exchanged in position and orientation. Also, as used herein, the terms "substantially" and/or "about" mean that the specified dimension or parameter may be varied within an acceptable manufacturing tolerance for a given application. In one embodiment, the acceptable manufacturing tolerance is ±0.25%.

Figure 1:
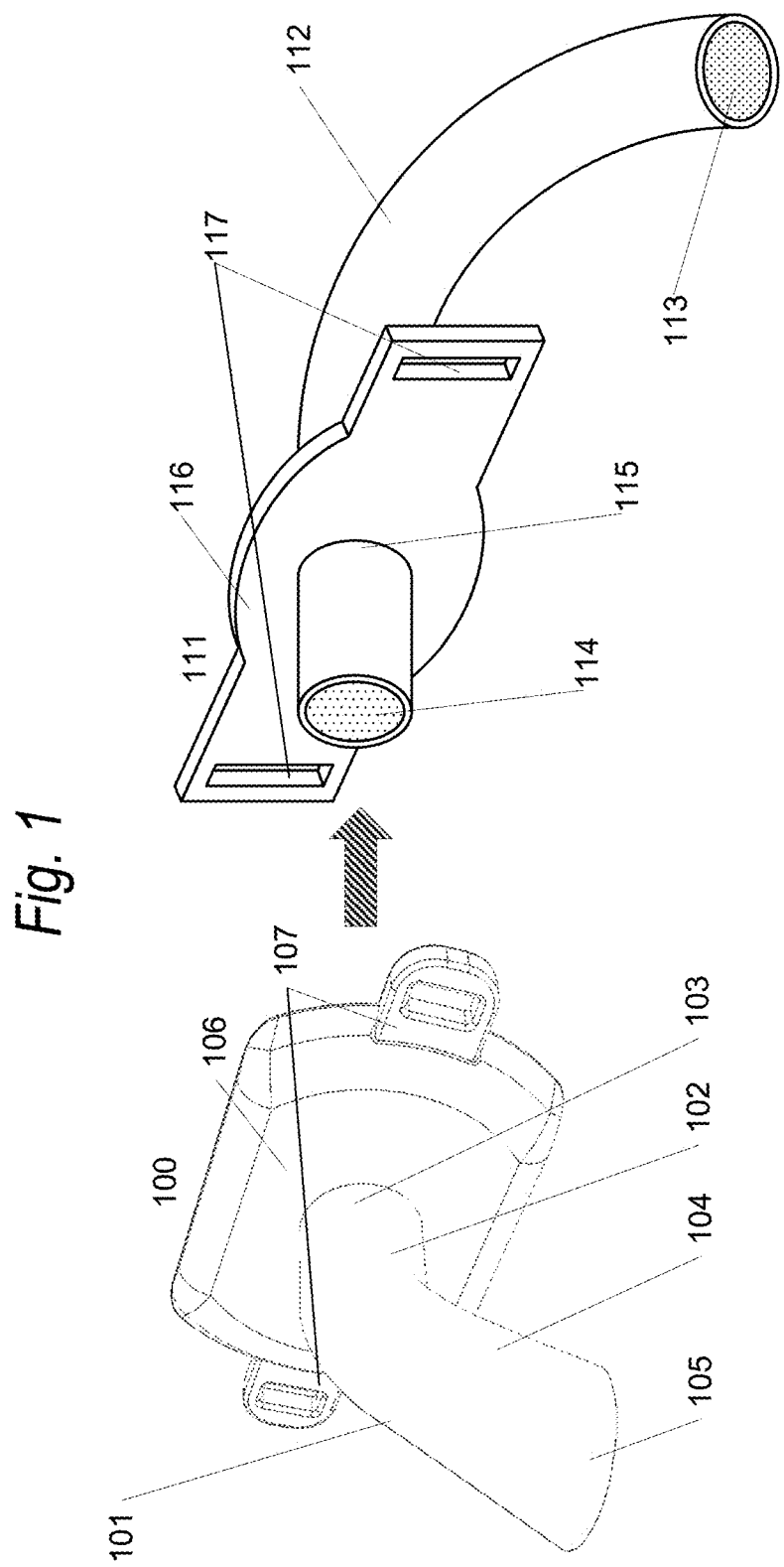
FIG. 1 is a perspective view of a tracheal tube attachment and a tracheal device.

FIG. 1 depicts how an embodiment of the tracheal tube attachment 100 may fit into an example of a tracheal device 111. The tracheal device 111 may consist of a tube 112 having an open proximal end 113 and an open distal end 114. The tube 112 may fit through a circular hole 115 in the center of a plate 116 having two embedded slots 117 that may be fitted with straps for securing the tracheal device 111 to the person's neck. The proximal end 113 of the tracheal device 111 may be inserted into the person's trachea via a stoma in the person's neck while the distal end 114 of the tracheal device 111 remains outside the person's neck. The tracheal tube attachment 100 may attach to the distal end 114 of the tracheal device 111 to prevent water and other unwanted materials from entering the tracheal device 111 through the opening at its distal end 114.

Figure 2:
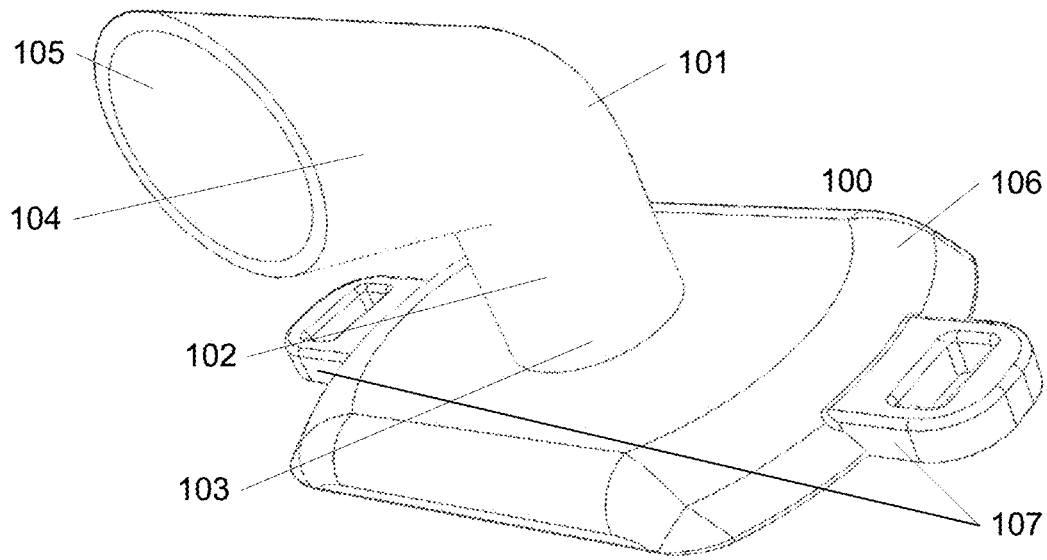
FIG. 2 is a perspective view of a tracheal tube attachment with a generally rectangular plate having two loops.
Figure 3:
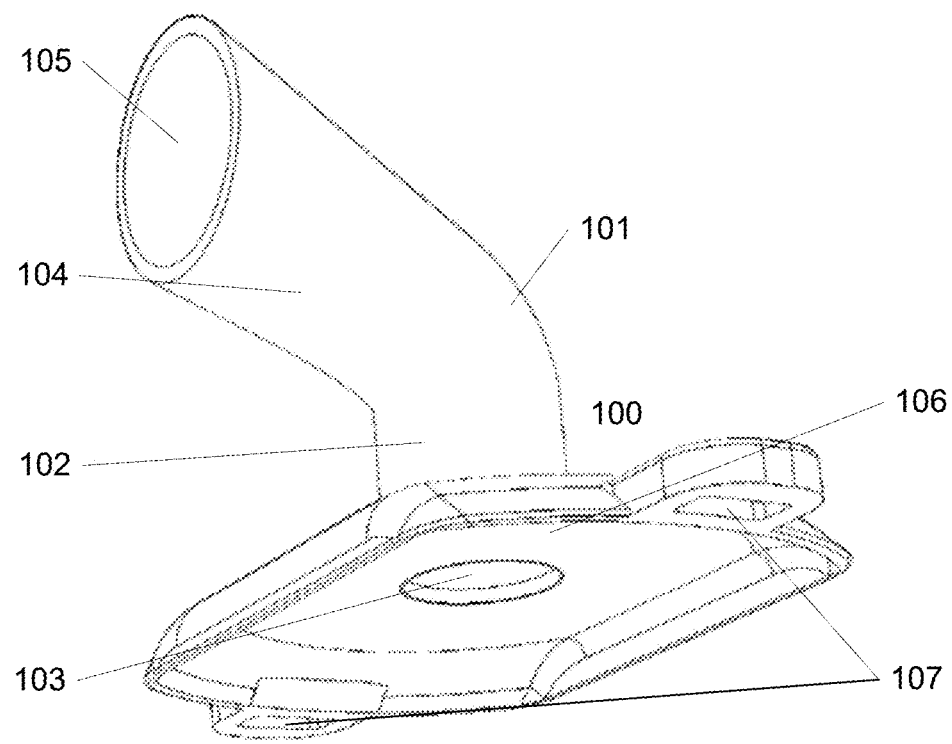
FIG. 3 is another perspective view of the tracheal tube attachment shown in FIG. 2 showing the bottom side of the plate.

FIGS. 1-3 depict a first embodiment of the present technology, comprising a tracheal tube attachment 100 for a tracheal device 111. The attachment 100 may be made from medical grade ABS plastic, although it is understood that other materials may be used in further embodiments. The attachment 100 may comprise a hollow tube 101 and a plate 106. The tube 101 may comprise a horizontal (when worn) proximal section 102 comprising a proximal end 103 and a distal section 104 comprising a distal end 105. The proximal section 102 may integrally connect to the distal section 104 at an intermediate point along the length of the tube 101 between the proximal end 103 and distal end 105. The proximal section 102 may have a consistent diameter along its length. The distal section 104 may have a diameter that increases towards the distal end 105, starting at a diameter equal to the diameter of the proximal section 102 at the intermediate point. The distal section may therefore form a hollow cone shape with a wider distal end. Because the suction force decreases as the diameter increases, this design provides the benefit of further preventing the person from inhaling water and other unwanted materials into the trachea while simultaneously increasing airflow. The distal section 104 may extend downwards at an angle of greater than 0 and less than or equal to 90 degrees relative to the orientation of the proximal section 102. It is understood that the angle may be 0 and greater than 90 degrees in further embodiments.

The proximal end 103 of the tube 101 may be integrally connected with the center of the plate 106. The plate 106 may have a circular hole in its center with the same diameter as the proximal end 103 of the tube 101 so that the plate 106 would not block the opening of the tube 101 at the proximal end 103.

The plate 106 may be flat and generally rectangular and curve away from the distal end 105 and towards the tracheal device 111 at its outer edges. It is understood that the plate 106 may be of other shapes in further embodiments. For example, the plate 106 may be completely flat and not have curvature on its outside edges. Alternatively, the plate 106 may have a dome shape. In further embodiments, the plate 106 may also have a shape that matches any indentations found around the distal end 114 of the tracheal device 111 so that the plate 106 would closely wrap around and cover up an area around the distal end 114 of the tracheal device 111. This design may further prevent unwanted materials from getting into a person's trachea via the distal end 114 of the tracheal device 111.

The plate 106 may also have two loops 107 that are integrally connected to the outer edge of the plate 106 at opposite sides to each other. The loops 107 may be placed so that an imaginary line connecting the two loops 107 would be perpendicular to the downward orientation of the distal section 104 of the tube 101. These loops 107 may be fitted with straps 110 for securing the tracheal tube attachment 100 to the tracheal device 111 and/or the person's body. The straps 110 can be a single piece that loops around the person's neck or small pieces of Velcro that stick onto the tracheal device 111, or any other appropriate means for securing the attachment 100 to the person's body.

Figure 4:
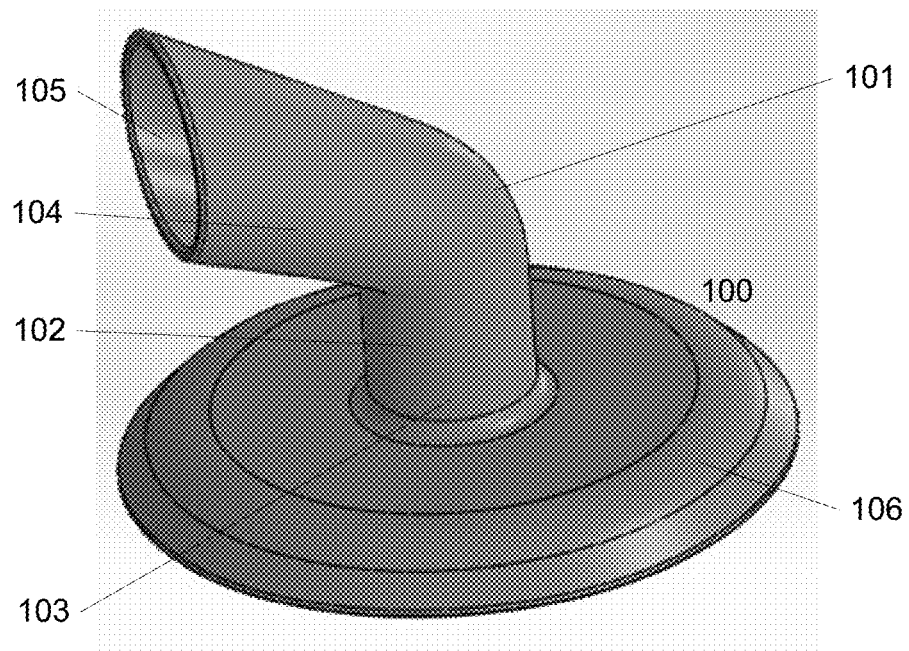
FIG. 4 is a perspective view of a tracheal tube attachment with a circular plate.
Figure 5:
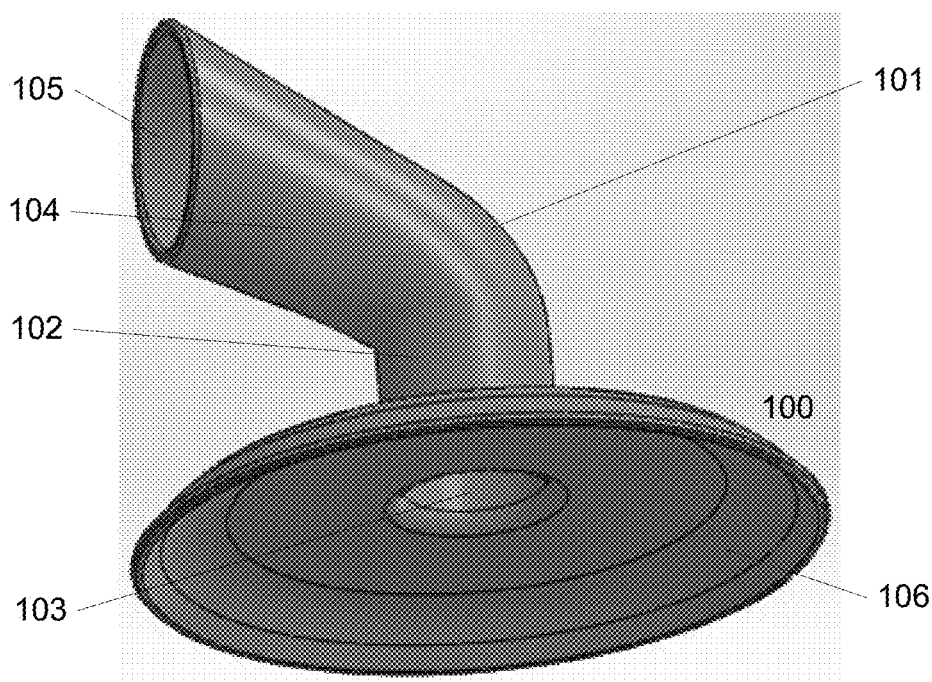
FIG. 5 is another perspective of the tracheal tube attachment shown in FIG. 4 showing the bottom side of the plate.
Figure 6:
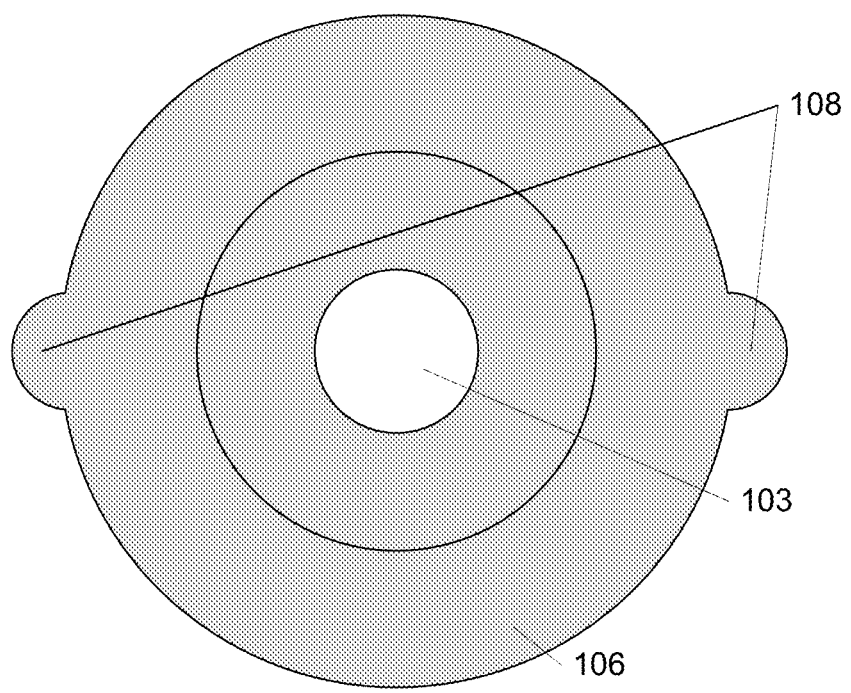
FIG. 6 is a cross-sectional view through the proximal section showing a circular tracheal tube attachment plate having two tabs.
Figure 7:
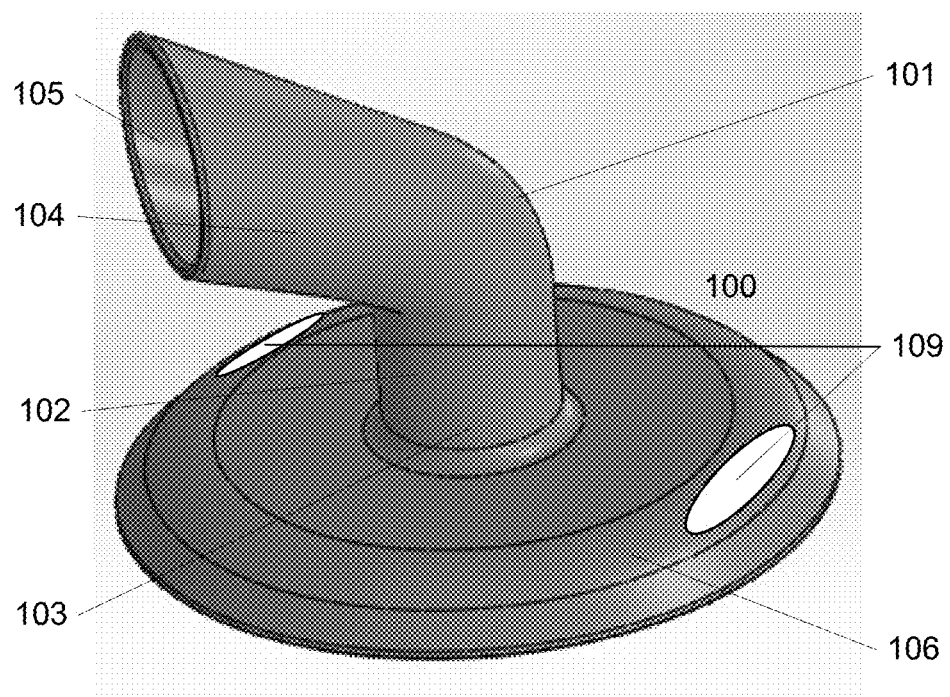
FIG. 7 is a perspective view of a tracheal tube attachment with two embedded slots.
Figure 8:
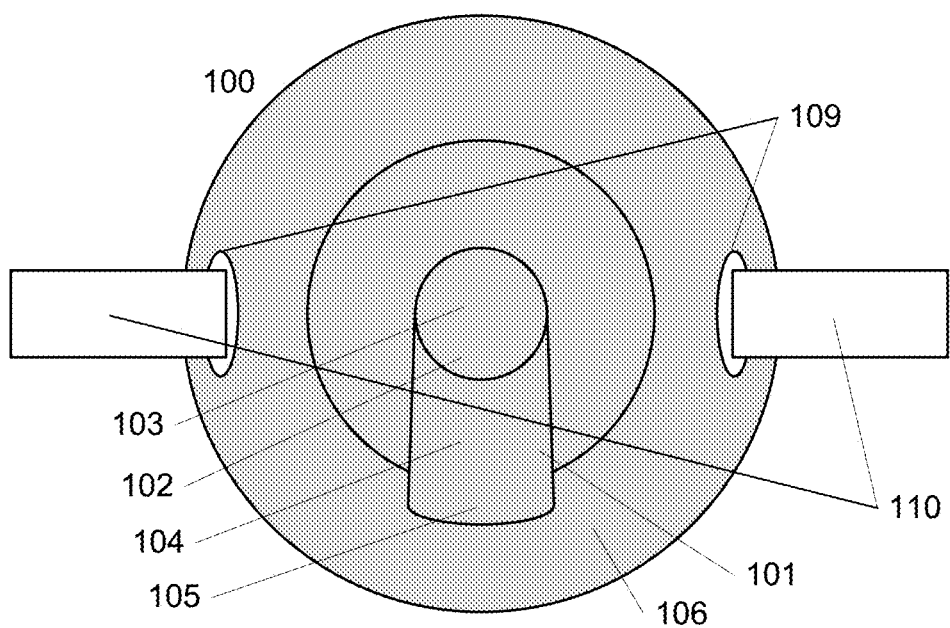
FIG. 8 is a front view of the tracheal tube attachment shown in FIG. 7 with two straps fitted through its embedded slots.

FIGS. 4-5 depict a second embodiment where the base 106 is circular and does not have any features protruding from its outer edges. In this embodiment, the tracheal tube attachment 100 may be secured to the tracheal device 111 or the person's body using an adhesive such as tape. FIG. 6 depicts a third embodiment where two tabs 108 protrude outwards from opposing ends of the outer edge of the plate 106. An adhesive such as tape can stick to the tabs 108 for securing the attachment to a tracheal device 110 and/or the person's body. FIGS. 7-8 depict a fourth embodiment where two slots 109 are embedded within a circular plate 106 on opposite sides. Straps 110 for securing the attachment 100 to a tracheal device 111 and/or to a person's body can loop through these slots 109.

We claim:

1. A tracheal tube attachment for a tracheal device, the tracheal device comprising a first plate configured to be positioned at a neck of a user, and a first tube, attached to the first plate, configured to extend through a stoma in the neck of the user, the tracheal tube attachment comprising:
   a second plate configured to fit around the first plate, and comprising a hole configured to receive an end of the first tube, through the second plate; and
   a second tube connected to the second plate, the second tube configured to be used external to the neck of the user and the second tube comprising a bend in two opposed walls of the second tube, the bend configured to prevent entry of water into the tracheal device and a trachea of the user, the second tube comprising:
      a proximal section affixed to the second plate and extending generally perpendicularly out from the second plate, the proximal section having an open proximal end open to the hole in the second plate; and
      a distal section having an open distal end, the proximal and distal sections connecting to each other at the bend, the bend positioning the open distal end downward to prevent entry of water into the open distal end, the distal section comprising a diameter that is the same as a diameter of the proximal section at a point where the distal section connects to the proximal section, the diameter of the distal section increasing continuously between a proximal end of the distal section and the distal end of the distal section.

2. The tracheal tube attachment as set forth in claim 1 wherein the proximal section has a consistent diameter along a length of the proximal section.

3. The tracheal tube attachment as set forth in claim 1 wherein the diameter of the proximal section is dimensioned for attaching to the first tube of the tracheal device.

4. The tracheal tube attachment as set forth in claim 1 wherein the second plate is flat.

5. The tracheal tube attachment as set forth in claim 4 wherein the second plate is circular.

6. The tracheal tube attachment as set forth in claim 5 wherein outer edges of the second plate curve away from the distal end and around outer edges of the first plate of the tracheal device.

7. The tracheal tube attachment as set forth in claim 4 wherein the second plate is generally rectangular.

8. The tracheal tube attachment as set forth in claim 7 wherein outer edges of the second plate curve away from the distal end and around outer edges of the first plate of the tracheal device.

9. The tracheal tube attachment as set forth in claim 1 wherein the second plate has a dome shape curving away from the distal end and towards the tracheal device.

10. The tracheal tube attachment as set forth in claim 1 wherein the second plate further comprises two loops attached to outer edges of the second plate on opposite sides.

11. The tracheal tube attachment as set forth in claim 10 wherein the loops are fitted with straps for securing the second plate to either the tracheal device and/or to a body of the user.

12. The tracheal tube attachment as set forth in claim 1 wherein the second plate further comprises two slots embedded in outer edges of the second plate on opposite sides.

13. The tracheal tube attachment as set forth in claim 12 wherein the slots are fitted with straps for securing the second plate to either the tracheal device and/or to a user's body.

14. The tracheal tube attachment as set forth in claim 1 wherein the second plate further comprises two tabs attached to outer edges of the second plate on opposite sides.

15. The tracheal tube attachment as set forth in claim 14 wherein an adhesive is attached to the two tabs for securing the two tabs to either the tracheal device or to a body of the user.

16. A tracheal tube attachment for a tracheal device, the tracheal device comprising a first plate configured to be positioned at a neck of a user, and a first tube, attached to the first plate, configured to extend through a stoma in the neck of the user, the tracheal tube attachment comprising:
   a second plate having a flat central portion with outer edges configured to curve around edges of the first plate, the second plate comprising a hole configured to receive an end of the first tube, through the second plate; and
   a second tube connected to the second plate, the second tube configured to be used external to the neck of the user and the second tube comprising a bend in two opposed walls of the second tube, the bend configured to prevent entry of water into the tracheal device and a trachea of the user, the second tube comprising:
      a proximal section affixed to the second plate and having an open proximal end open to the hole in the second plate, the proximal section having a consistent diameter along a length of the proximal section; and
      a distal section having an open distal end, the proximal and distal sections connecting to each other at the bend, the bend positioning the open distal end downward with respect to gravity to prevent entry of water into the open distal end, the distal section comprising a diameter that is the same as the diameter of the proximal section at a point where the distal section connects to the proximal section, the diameter increasing towards the distal end.

17. The tracheal tube attachment as set forth in claim 16, wherein the second plate further comprises two loops attached to the outer edges of the second plate on opposite sides.

18. The tracheal tube attachment as set forth in claim 17 wherein the loops are fitted with straps for securing the second plate to either the tracheal device and/or to a body of the user.

* * * * *